(12) United States Patent
Marino

(10) Patent No.: US 10,813,878 B2
(45) Date of Patent: Oct. 27, 2020

(54) ORAL HEALTH COMPOSITION

(71) Applicant: Monica Nikita Marino, Riverside, CT (US)

(72) Inventor: Monica Nikita Marino, Riverside, CT (US)

( * ) Notice: Subject to any disclaimer, the term of this patent is extended or adjusted under 35 U.S.C. 154(b) by 0 days.

(21) Appl. No.: 15/909,376

(22) Filed: Mar. 1, 2018

(65) Prior Publication Data

US 2019/0269607 A1 Sep. 5, 2019

(51) Int. Cl.
| | |
|---|---|
| *A61K 8/9789* | (2017.01) |
| *A61K 8/19* | (2006.01) |
| *A61Q 11/00* | (2006.01) |
| *A61K 8/34* | (2006.01) |
| *A61K 8/92* | (2006.01) |
| *A61K 8/9794* | (2017.01) |

(52) U.S. Cl.
CPC .............. *A61K 8/9789* (2017.08); *A61K 8/19* (2013.01); *A61K 8/345* (2013.01); *A61K 8/922* (2013.01); *A61K 8/9794* (2017.08); *A61Q 11/00* (2013.01)

(58) Field of Classification Search
None
See application file for complete search history.

(56) References Cited

U.S. PATENT DOCUMENTS

2017/0281538 A1* 10/2017 Golden ................ A61K 31/593

OTHER PUBLICATIONS

Sekar, Mahendran, and Noor Jasmin Shamsul Ariffin. "Formulation, Evaluation and Antibacterial Properties of Novel Polyherbal Toothpaste for Oral Care."*

Devaraj, Sharmila Devi, and Prasanna Neelakantan. "Curcumin-pharmacological actions and its role in dentistry." Asian Journal of Pharmaceutical Research and Health Care 6.1 (2014).*

* cited by examiner

*Primary Examiner* — John Pak
*Assistant Examiner* — Daniel L Branson

(57) ABSTRACT

An ingestible oral health composition has synergistic proportions of active ingredients consisting of: baking soda; guava leaves; turmeric; black pepper; erythritol or xylitol; coconut oil; and vegetable glycerin with a natural flavor extract. The oral health composition may be in the form of a tablet, a powder, a paste, or a suspension. The oral health composition provides superior cleaning and control of oral health problems. The oral health composition can be ingested to provide health benefits to the entire body.

11 Claims, No Drawings

ORAL HEALTH COMPOSITION

BACKGROUND OF INVENTION

Antimicrobial toothpaste has been proposed for the treatment of gum disease using a wide variety of antimicrobial agents, but none has achieved widespread commercial use. The formulation of antimicrobial toothpaste must satisfy several, often conflicting, requirements. The antimicrobial toothpaste must provide a statistically significant therapeutic effect in humans. Also, the antimicrobial toothpaste must not be irritating to the oral cavity. The use of antimicrobial agents in the oral cavity is often accompanied by unacceptable irritation of the oral cavity. While such harsh antimicrobial agents may be safely applied by a dentist on an infrequent basis as part of an annual check-up or the like, they are unsuited for daily use by consumers in the form of over-the-counter (OTC) toothpastes. To be commercially successful, an antimicrobial mouthwash must have the properties essential to OTC toothpastes, such as storage stability, long shelf life, acceptable taste, decent mouthfeel and the other characteristics.

Dental plaque is harmful to the gums. Secretions from the bacteria associated with dental plaque include acid, which is involved in the formation of caries, and enzymes and endotoxins, which can irritate the gums and cause gingivitis. An OTC antimicrobial toothpaste that is safe, effective and of acceptable cosmetic properties, particularly taste, the present invention makes available to the consumer the means for conveniently promoting oral hygiene in general and for reducing dental plaque and gingivitis and will create innumerable benefits when is ingested To this end an oral health composition that is antimicrobial and antiplaque, while being non-irritating remains a commercial target. Additionally, an antimicrobial dentifrice that treats and protects tooth enamel is desirable. An oral health composition that is ingested rather that expelled such that the same antimicrobial and protective effect can be provided to the internal organs of the human body.

BRIEF SUMMARY

Embodiments of the invention are directed to an ingestible oral health composition, comprising synergistic proportions of active ingredients consisting of: baking soda; guava leaves; turmeric; black pepper; erythritol or xylitol; coconut oil; and vegetable glycerin with a natural flavor extract. The natural flavor extract, though not limited to, can be an extract of peppermint, raspberry, or grapefruit. The synergistic proportions of active ingredients are 13 to 25 weight percent baking soda, 12 to 20 weight percent turmeric, 9 to 14 weight percent black pepper, 11 to 22 weight percent erythritol or xylitol, 12 to 15 weight percent coconut oil, and 3 to 4 percent vegetable glycerin, with the balance being the natural flavor extract. Weight percent values that are ten percent greater or lower than these optimal ranges may be used. The ingestible oral health composition can include inactive components selected from natural excipients, buffers, and fluids. The ingestible oral health composition can be in the form of a tablet, a powder, a paste, or a suspension.

In an embodiment of the invention, the ingestible oral health composition can be coated on or infused into a mouth cleaning device. The mouth cleaning device can be a toothpick, floss, scraper, or disposable brush.

An embodiment of the invention is directed to a method of cleaning the oral cavity, where a tablet, powder, paste, or suspension that comprising the ingestible oral health composition with synergistic proportions of active ingredients consisting of: baking soda; guava leaves; turmeric; black pepper; erythritol or xylitol; coconut oil; and vegetable glycerin with a natural flavor extract is contacted in the oral cavity of a user by chewing, brushing gargling, picking, or flossing. The user can be a human person or can be any mammal, such as a dog or cat. It is intended that the user will effectively swallow at least a portion of the ingestible oral health composition and the composition is intended to be swallowed to as large an extent as possible to extend the health benefits to the entire body.

DETAILED DISCLOSURE

An embodiment of the present invention is directed to a highly effective antimicrobial, antioxidant, anti-inflammatory oral health composition. The oral health composition is a synergistic blend of active compounds derived from natural sources such that they may be ingested by the user. The oral health composition includes extracts and isolated components from turmeric, black pepper, guava leaves, peppermint, grapefruit, raspberry extract, xylitol, erythritol, coconut oil and vegetable glycerin. Other natural ingredients may be included. These oral health compositions are suitable for daily use alone or with another oral care hygiene product, such as dentifrice and mouth rinse formulations.

The oral health compositions, according to an embodiment of the invention, inhibit growth of various oral bacteria that are implicated in forming plaque and causing oral diseases. The oral health composition of the present invention is applied to one or more oral surfaces in the oral cavity and promotes overall oral health, inhibiting plaque formation, gingivitis, periodontitis, and other oral health problems. For example, in an embodiment of the present invention, the oral care composition comprises an orally acceptable delivery carrier as a tablet as they dissolve or are masticated, but provide a safe and effective amount of the toothpaste compounds. It has been observed that the compounds have intrinsic properties as anti-inflammatory activity, antioxidant activity, and is highly efficacious against bacteria, including those that form plaque. Thus, the oral health compositions according to embodiments of the invention provide multiple oral care benefits simultaneously, and provide additional health support upon ingestion.

The compositions according to the present invention comprise compounds found in turmeric (curcumin), black pepper (piperine), guava leaves, xylitol or erythritol, pure 100% organic coconut oil, 100% natural vegetable glycerin, and peppermint extract, grapefruit extract, and/or raspberry extract. Sodium bicarbonate is included to further promote enamel protection. The extracts may be in liquid or dried powder forms.

In an embodiment of the invention, a proper mix of tea guava leaves, appropriate amount of turmeric, black pepper, the flavor enhancing extract of peppermint, grapefruit or raspberry, the xylitol or erythritol, the pure 100% organic coconut oil, 100% organic vegetable glycerin, and added sodium bicarbonate are concentrated in a paste, which is subjected to drying over time, for example, but not limited to one to two days. These compounds contribute to efficacy in a variety of areas and functionality. The oral health compositions comprising the paste have active ingredients that are effective as anti-inflammatory agents, as well.

Inflammation in the oral cavity is often secondary to traumatic injury from foreign bodies or gavage procedure or to necrosis from chemical agents. Infectious agents, usually opportunistic organisms, such as bacteria and fungi and promote these inflammations. In National Toxicology Program (NTP) studies, five standard categories of inflammation are identified, these categories are: acute; suppurative; chronic; chronic active; and granulomatous. In acute inflammation, the predominant infiltrating cell is the neutrophil, though fewer macrophages and lymphocytes may also be present. There may also be evidence of edema or hyperemia. The neutrophil is also the predominant infiltrating cell type in suppurative inflammation, but the neutrophils are aggregated, and many of them are degenerate (suppurative exudate). Cell debris results from the resident cell populations and from infiltrating leukocytes, proteinaceous fluid containing fibrin, macrophages, lymphocytes, or plasma cells, and, possibly, infectious agents present within the exudate. Grossly, these lesions are characterized by the presence of pus. The tissue surrounding the exudate may contain fibroblasts, fibrous connective tissue, and mixed inflammatory cells, depending on the chronicity of the lesion. Lymphocytes predominate in chronic inflammation. Lymphocytes also predominate in chronic active inflammation, but there are also a significant number of neutrophils. Both lesions may contain macrophages. Granulomatous inflammation is another form of chronic inflammation, but this diagnosis requires the presence of a significant number of aggregated, large, activated macrophages, epithelioid macrophages, or multinucleated giant cells. (See, for example, https://ntp.niehs.nih.gov/nnl/alimentary/oral_mucosa/inflamm/oral-mucosa-inflammation_508.pdf In an embodiment of the invention, a method of treatment employing the oral health composition, according to an embodiment of the invention, is administered in the form of a tablet that when mixed with the saliva for cleaning the teeth, releases the composition's benefits to sites of inflamed oral tissue. In embodiments of the invention, the active anti-inflammatory ingredients of the oral health composition synergistically inhibit action and formation of multiple inflammatory mediators. Each respective mediator has a different mechanism in the pathogenesis of a disease. The inflammatory mediators do not react with or diminish the efficacy and bioavailability of the components.

The oral health composition includes a compound mix that significantly reduces the production of one or more inflammatory mediators. The compound mix composition prevents the over-expression of one or more inflammatory mediators, preventing an intrinsic mechanism for chronic disease. The concentration of the active ingredients is typically dependent upon the form of the oral health composition.

The active components of the oral health composition prevent or treat conditions and disorders of hard or soft tissue of the oral cavity and provide a cosmetic benefit. Consequently, the compositions of the present invention may be used for the treatment or prevention of systemic disorders, which affect the entire body, rather than a single organ or body part. The use of the oral health composition benefits the user's health by a reduced development of systemic diseases, such as cardiovascular disease, stroke, and diabetes.

Oral care components of oral health compositions include whitening agents, anticaries agents, tartar control agents, periodontal actives, abrasives, breath freshening agents, tooth, salivary stimulants, anti-adhesion agents, and plaque dispersing agents. The oral health composition avoids all damaging health components of fluoride ions or other a fluorine providing component. Thus, the oral health composition comprises orally acceptable agents to reduce gingivitis, plaque, calculus, caries or sensitivity and the composition components mix is a breath-freshening agent. Antibacterial agent included in the oral health composition of the present invention is xylitol and/or erythritol.

The anticaries agent, xylitol $C_5H_{12}O_5$, is a five-carbon sugar alcohol that is not endogenously produced by humans. Xylitol is used as a diabetic sweetener as it is roughly as sweet as sucrose with 33% fewer calories. Xylitol is naturally found in many fruits, including strawberries, plums, and raspberries and in vegetables such as cauliflower. A diet that commonly includes fruit and vegetable consumption allows the human body to processes 15 grams of xylitol per day. Xylitol can be produced industrially starting from primary matters rich in xylan which is hydrolyzed to obtain xylose. It is extracted from hemicelluloses present in the corn raids, almond hulls, birch bark, or as a by-product of hard wood shavings or paper pulp. Of all polyols, it is the one that has the sweetest flavor (it borders that of saccharose). Xylitol gives a strong refreshing impression, making xylitol an ingredient of choice for the sugarless chewing gum industry. In addition to use in confectionery, xylitol is used in some mouthwashes and toothpastes.

Erythritol, $C_4H_{10}O_4$, occurs widely in nature and has been found to occur naturally in wine, sake, beer, watermelon, pear, grape and soy sauce. Erythritol exists endogenously in the tissues and body fluids of humans and animals. Erythritol is absorbed from the proximal intestine by passive diffusion in a manner similar to that of many low molecular weight organic molecules that do not have associated active transport systems, the rate of absorption being related to their molecular size. Erythritol passes through the intestinal membranes at a faster rate than larger molecules such as mannitol or glucose. In people with diabetes, erythritol also has been shown to be rapidly absorbed and excreted unchanged in the urine. Following absorption, ingested erythritol is rapidly distributed throughout the body and has been reported to occur in hepatocytes, pancreatic cells, and vascular smooth muscle cells. Erythritol also has been reported to cross the human placenta and to pass slowly from the plasma into the brain and cerebrospinal fluid. (National Center for Biotechnology Information. PubChem Compound Database: CID=6912, https://pubchem.ncbi.nlm.nih.gov/compound/6912; and CID=222285, https://pubchem.ncbi.nlm.nih.gov/compound/222285.

Turmeric and black pepper provide antioxidant properties and desensitization to pain receptors. Piperine in the black pepper increases the bioavailability of the turmeric and other components of the oral health composition. Turmeric reduces gingivitis, is anti-plaque, and suppresses periodontitis, oral lichen planus and ulceration. Extracts of guava leaves contain phenolic compounds that helps to prevent and cure gum infections, bad breath, and mouth ulcers. These phenolic compounds are antibacterial to aid against cavities. Coconut oil contains lauric acid that is antibacterial, particularly against the oral bacteria *Streptococcus mutans* that causes bad breath, tooth decay and gum disease. Glycerin is anti-bacterial, penetrate cavities, and reaches under the gum line to remove periodontal disease bacteria.

The combination of these ingredients is much more effective than they are individually. The oral health compositions according to embodiments of the invention are dramatically effective for oral health. It has been discovered that when the active ingredients are in particular proportions, the results are superior to typical commercial formulations, yet are safe and beneficial to the whole person and should be ingested after treating the oral cavity for at least 30 seconds, for example, but not limited to one to three minutes. The synergistic formulations, according to an embodiment of the invention has 13 to 25 weight percent baking soda, 8 to 12, weight percent guava leaves, 12 to 20 weight percent turmeric, 9 to 14 weight percent black pepper, 11 to 22 weight percent erythritol or xylitol, 12 to 15 weight percent coconut oil, and 3 to 4 percent vegetable glycerin, with the balance being the natural flavor extract.

In addition, the antibacterial agents of the oral health compositions are compounds to prevent plaque formation. These antiplaque agents operate by an anti-adhesion mechanism and by a plaque disrupting mechanism. The oral health composition is regularly applied to an oral surface, preferably on a daily basis. The oral health composition is applied to the buccal surfaces at least 1 to 3 times daily.

The oral health compositions of the present invention may be prepared by suitably mixing the ingredients. For instance, in the preparation of a toothpaste tablet, the active ingredients are mixed, agitated, and heated to 110° to 120° F. The heated mixture is then cooled to less than 100° F. and left to dry to form a powder. The powder can be used as a tooth powder. The powder can be compressed into a tablet for chewing. The tablets can be of any suitable size and shape and packed into a suitable container. The tablets can be provided as an after dinner mint for chewing and providing the oral and other health benefits. The pre-dried wet oral health composition or a rehydrated powder oral health composition can be packaged as toothpaste in tubes. The oral health composition can be infused into vehicles such as toothpicks and flosses. Formulation can be in the form of a solution, suspension, or emulsion for rinsing the mouth. These compositions can be ingested rather than spit or otherwise removed from the mouth. The ingestible oral health composition can include inactive components selected from natural excipients, buffers, and fluids. Excipients include fillers, binders, flow agents, coatings and glazes, and colorants, as appreciated by those of skill in the art. Buffers can be used to assure a desired pH of the ingestible oral health composition. Fluids are ingestible liquids, such as, but not limited to water, ethanol, and other vegetable oils.

The non-fluoride and anti-plaque toothpaste, according to an embodiment of the invention, has a consumer-acceptable taste in an orally acceptable dental vehicle. The oral health compositions of the present invention may be prepared in the form of a paste of uniform color or the form of tablets. The antimicrobial agents used in the oral health compositions are antimicrobial, safe and effective in the treatment of plaque and gingivitis in humans. Antimicrobial, anti-inflammatory toothpastes, according to an embodiment of the invention contain components from any suitable source of edible botanical plants that can be ingested to maximize all the benefits of the ingredients, providing anti-inflammatory and antimicrobial to portions of the body outside of the mouth. If desired fluoride or fluoride providing ingredients can be included to the formulations, according to an embodiment of the invention.

The toothpaste tablets or paste, according to an embodiment of the invention, is contacted with the mouth by applying the toothpaste to the teeth, or chew it and brushed with the toothbrush, and it can be digested or spit. Brushing the teeth with the toothpaste or chewing the tablets of the present invention reduces the formation of dental plaque and gingivitis. The toothpaste or the chewing tablets provide excellent cosmetic properties, have a pleasant taste, and are stable upon storage.

METHODS AND MATERIALS

The following oral health compositions are for illustration of embodiments of the invention and is not limiting. All amounts and proportions referred to herein and in the appended claims are by weight unless otherwise indicated.

Original Flavored Tablets

A dentifrice formulation is prepared to contain the active ingredients by weight percent: 15% of Baking soda, 21% guava leaves, 28% of Erythritol, 28% of Coconut Oil, 4% of 100% Vegetable Glycerin The oral health composition is prepared by suitably mixing the ingredients. For instance, in the preparation of a toothpaste tablet, the active ingredients are added to a mixture. The combined ingredients are agitated and heated t 110° to 120° F. The heated mixture is then cooled to less than approximately 100° F. The resulting mix product is then left to dry, and the powder passed through the tablet machine to create the chewing tablets and packed into a suitable container. This formulation was effective, but inferior to subsequent formulations with the synergistic inclusion of turmeric and black pepper.

Raspberry Flavored Toothpaste

A dentifrice formulation is prepared to contain the active ingredients by weight percent: 23% of Baking soda, 14% of Turmeric, 10% of Black Pepper, 20% of Erythritol, 13% of Coconut Oil, 18% of Raspberry Extract, 3% of 100% Vegetable Glycerin.

Peppermint Flavored Tablets

A dentifrice formulation is prepared to contain the active ingredients by weight percent: 15% of Baking soda, 18% of Turmeric, 13% of Black Pepper, 13% of Erythritol, 14% of Coconut Oil, 23% of Peppermint Extract, and 4% of 100% Vegetable Glycerin.

The oral health composition is prepared by suitably mixing the ingredients. For instance, in the preparation of a toothpaste tablet, the active ingredients are added to a mixture, the mixture agitated and heated to 110° to 120° F. The heated mixture is then cooled to less than approximately 100° F. The resulting mix product is then left to dry, and the powder passed for the tablet machine to create the chewing tablets.

Grapefruit Flavored Tablets

A dentifrice formulation is prepared to contain the active ingredients: 23% of Baking soda, 14% of Turmeric, 10% of Black Pepper, 10% guava leaves 20% of Xylitol, 13% of Coconut Oil, 18% of Grapefruit extract, 3% of 100% Vegetable Glycerin.

The oral health composition is prepared by suitably mixing the ingredients. For instance, in the preparation of a toothpaste tablet, the active ingredients are added to a mixture. The combined ingredients are agitated and heated t 110° to 120° F. The heated mixture is then cooled to less than approximately 100° F. The resulting mix product is then left to dry, and the powder passed through the tablet machine to create the chewing tablets and packed into a suitable container.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. An ingestible oral health composition comprising:
active ingredients in synergistic proportions wherein the active ingredients consist of:
13 to 25 weight percent baking soda,
8 to 12 weight percent guava leaves,
12 to 20 weight percent turmeric,
9 to 14 weight percent black pepper,
11 to 22 weight percent erythritol or xylitol,
12 to 15 weight percent coconut oil, and
3 to 4 weight percent vegetable glycerin, with the balance being natural flavor extract, wherein the weight percent is determined based upon the total weight of the active ingredients;
wherein the active ingredients can be incorporated from fresh, powdered, or extracted forms, and
wherein the composition is for application to one or more surfaces in the oral cavity.

2. The ingestible oral health composition according to claim 1, wherein the natural flavor extract is an extract of peppermint, raspberry, or grapefruit.

3. The ingestible oral health composition according to claim 1, further comprising inactive components selected from the group consisting of excipients, buffers, and fluids.

4. The ingestible oral health composition according to claim 1, wherein the ingestible oral health composition is in the form of a tablet, a powder, a paste, or a suspension.

5. The ingestible oral health composition according to claim 1, wherein the ingestible oral health composition is coated on or infused into a mouth cleaning device.

6. The ingestible oral health composition according to claim 5, wherein the mouth cleaning device is a toothpick, a floss, a scraper, or a disposable brush.

7. A mouth cleaning device coated or infused with an ingestible oral health composition comprising:
active ingredients in synergistic proportions wherein the active ingredients consist of:
13 to 25 weight percent baking soda,
8 to 12 weight percent guava leaves,
12 to 20 weight percent turmeric,
9 to 14 weight percent black pepper,
11 to 22 weight percent erythritol or xylitol,
12 to 15 weight percent coconut oil, and
3 to 4 weight percent vegetable glycerin, with the balance being natural flavor extract, wherein the weight percent is determined based upon the total weight of the active ingredients;
wherein the active ingredients can be incorporated from fresh, powdered, or extracted forms; and
wherein the mouth cleaning device comprises a toothpick, a floss, or a disposable brush.

8. A method of cleaning an oral cavity comprising:
providing a powder, a paste, a multiplicity of tablets, or a suspension comprising the oral health composition of claim 1 comprising:
active ingredients in synergistic proportions wherein the active ingredients consist of:
13 to 25 weight percent baking soda,
8 to 12 weight percent guava leaves,
12 to 20 weight percent turmeric,
9 to 14 weight percent black pepper,
11 to 22 weight percent erythritol or xylitol,
12 to 15 weight percent coconut oil, and
3 to 4 weight percent vegetable glycerin, with the balance being natural flavor extract, wherein the weight percent is determined based upon the total weight of the active ingredients;
wherein the active ingredients can be incorporated from fresh, powdered, or extracted forms;
contacting the powder, the paste, the tablet, or the suspension comprising the ingestible oral health composition with the oral cavity of a mammal; and
optionally, ingesting at least a portion of the ingestible oral health composition.

9. The method according to claim 8, wherein the natural flavor extract is an extract of peppermint, raspberry, or grapefruit.

10. The method according to claim 8, wherein contacting is chewing, brushing, gargling, picking, flossing, scraping, or any combination thereof.

11. The method according to claim 8, wherein contacting is for at least 30 seconds.

\* \* \* \* \*